(12) United States Patent
Brunner et al.

(10) Patent No.: US 9,492,198 B2
(45) Date of Patent: Nov. 15, 2016

(54) CLAMP FOR EXTERNAL FIXATION

(75) Inventors: Peter Brunner, Muri bei Bern (CH); Marcel Fuhrer, Deitingen (CH)

(73) Assignee: DEPUY SYNTHES PRODUCTS, INC., Raynham, MA (US)

(*) Notice: Subject to any disclaimer, the term of this patent is extended or adjusted under 35 U.S.C. 154(b) by 2379 days.

(21) Appl. No.: 11/318,938

(22) Filed: Dec. 22, 2005

(65) Prior Publication Data
US 2006/0255521 A1 Nov. 16, 2006

Related U.S. Application Data

(63) Continuation of application No. PCT/CH03/00424, filed on Jun. 26, 2003.

(51) Int. Cl.
*A61B 17/60* (2006.01)
*A61B 17/00* (2006.01)
*A61B 17/64* (2006.01)

(52) U.S. Cl.
CPC ......... *A61B 17/645* (2013.01); *A61B 17/6466* (2013.01)

(58) Field of Classification Search
CPC ............... A61B 17/60–17/663; A61B 17/7049–17/7052
USPC ............. 606/54–59, 259, 260, 277; 403/385, 403/395
IPC ........................................... A61B 17/60
See application file for complete search history.

(56) References Cited

U.S. PATENT DOCUMENTS 4,718,151 A * 1/1988 LeVahn et al. ............. 24/535
5,190,546 A * 3/1993 Jervis ...................... 606/78
(Continued)

FOREIGN PATENT DOCUMENTS

| EP | 1 016 380 A | 7/2000 |
| EP | 1 016 381 A | 7/2000 |
| WO | WO 2004/112625 A1 | 12/2004 |

OTHER PUBLICATIONS

International Search Report for International Application No. PCT/CH/2003/00424, mailed Mar. 4, 2004. German language version.
(Continued)

*Primary Examiner* — Jacqueline Johanas
(74) *Attorney, Agent, or Firm* — Fay Kaplun & Marcin, LLP

(57) ABSTRACT

A device for detachably clamping fastening elements in a surgical fixing or repositioning device. The device may a rod with a longitudinal axis. A first and second pair of clamping jaws may be operably associated with the rod. Each pair of clamping jaws may have a side surface as well as an inner clamping jaw and an outer clamping jaw, which may have indentations forming a channel. The channels may be opened towards the side surface of the clamping jaws. A fastening means may be positioned in the channels by pushing the fastening means into the openings in the side surface in a direction which may be at an angle with respect to the longitudinal axis of the rod. An elastic element may be positioned between the inner and outer clamping jaws of at least one pair of clamping jaws so as to resist movement of the inner and outer clamping jaws with respect to each other as a fastening means is inserted therebetween. A clamping element may engage the rod and may be used to fix the orientation of the clamping jaws and fastening means with respect to each other.

29 Claims, 3 Drawing Sheets

(56) References Cited

U.S. PATENT DOCUMENTS

| | | | |
|---|---|---|---|
| 5,741,252 A * | 4/1998 | Mazzio et al. | 606/54 |
| 5,752,954 A * | 5/1998 | Mata et al. | 606/59 |
| 5,921,985 A * | 7/1999 | Ross et al. | 606/59 |
| 6,022,348 A * | 2/2000 | Spitzer | 606/54 |
| 6,332,883 B1 | 12/2001 | Zucherman et al. | |
| 6,342,054 B1 * | 1/2002 | Mata | 606/59 |
| 6,375,458 B1 * | 4/2002 | Moorleghem et al. | 433/2 |
| 6,616,664 B2 * | 9/2003 | Walulik et al. | 606/57 |
| 6,702,814 B2 * | 3/2004 | Walulik et al. | 606/57 |
| 2001/0028148 A1 * | 10/2001 | White | 277/630 |
| 2002/0013586 A1 * | 1/2002 | Justis et al. | 606/61 |
| 2002/0026190 A1 * | 2/2002 | Walulik et al. | 606/57 |
| 2002/0165543 A1 * | 11/2002 | Winquist et al. | 606/54 |
| 2003/0149429 A1 * | 8/2003 | Ferrante et al. | 606/59 |
| 2005/0171539 A1 * | 8/2005 | Braun et al. | 606/61 |
| 2006/0212068 A1 * | 9/2006 | Boylan et al. | 606/200 |

OTHER PUBLICATIONS

International Search Report for International Application No. PCT/CH/2003/00424, mailed Mar. 4. 2004, English translation of German version.

International Preliminary Examination Report for International Application No. PCT/CH/2003/00424. completed Sep. 21, 2005. German language version.

International Preliminary Examination Report for International Application No. PCT/CH/2003/00424, completed Sep. 21. 2005. English translation of German version.

\* cited by examiner

CLAMP FOR EXTERNAL FIXATION

CROSS-REFERENCE TO RELATED APPLICATION

This application is a continuation of pending International Patent Application PCT/CH2003/000424, filed Jun. 26, 2003, which is incorporated by reference herein in its entirety.

FIELD OF THE INVENTION

The present invention relates to a clamp for external fixation and, more particularly, to a device for detachably clamping fastening elements in a surgical fixing or repositioning device.

BACKGROUND OF THE INVENTION

A double jaw connection for elements of an external fixator is known in the art. For example, DE 295 12 917 to Jaquet shows a layered arrangement of two pairs of clamping jaws, which consists of an upper outer clamping jaw and an upper inner clamping jaw, as well as a lower outer clamping jaw and a lower inner clamping jaw. The four clamping jaws are disposed on a central clamping shaft. Between the pairs of clamping jaws, that is, between the two inner clamping jaws, a coil spring is inserted. The coil spring causes the two inner clamping jaws to be pressed apart and pressed against the outer clamping jaws. The clamping jaws are constantly held together with the help of a locking device which acts against the action of the coil spring or elastic means. At the clamping surfaces between each pair of clamping jaws, indentations are provided which form a passage transverse to the clamping shaft for fastening rods or connectors of the external fixator. These passages are open to the outside and enable fastening rods or connectors to be inserted by exerting pressure in the opening of the clamping jaw in the respective passage against the action of the elastic means. After the fastening rods or connectors have snapped into the passages, but prior to the clamping jaws being prevented from articulating with respect to each other, the rods and connectors are held in position by the action of the elastic means.

One disadvantage of this construction is that the coil spring is disposed between the pairs of clamping jaws and, therefore, may not be readily accessible. Moreover, since the spring force depends upon the position of locking device such as a nut, the spring force is not constant. A coil spring is also subject to high fatigue. Therefore, it is desirable to provide an improved device for detachable clamping or fastening elements such as rods, retractors, rings or bone screws. In particular, it is desirable to provide a clamp which allows for independent operation of pairs of clamping jaws, has fewer components than existing devices so that simple operation and cleaning is possible, and has a constant spring force even without actuation of a nut/screw.

SUMMARY OF THE INVENTION

A clamping device may have a rod comprising a longitudinal axis, a first end and a second end; a first pair of clamping jaws operably associated with the rod, the first pair of clamping jaws having an inner clamping jaw and an outer clamping jaw; a second pair of clamping jaws operably associated with the rod, the second pair of clamping jaws having an inner clamping jaw and an outer clamping jaw; and a first elastic element having an axis, the first elastic element positioned between the inner and outer clamping jaws of the first pair of clamping jaws, wherein the axis of the first elastic element is spaced a distance from the longitudinal axis of the rod. The inner clamping jaw and the outer clamping jaw of the first pair of clamping jaws may have a bore, wherein the bore may receive the first elastic element. Moreover, a second elastic element may be positioned between the inner and outer clamping jaws of the second pair of clamping jaws. Each of the inner clamping jaw and the outer clamping jaw of the second pair of clamping jaws may have a bore, which may receive the second elastic element. At least one of the first and second elastic elements may have an axis which may be spaced a distance from the longitudinal axis of the rod.

The inner and outer jaws of the first and second pair of clamping jaws may comprise clamping surfaces, wherein the inner jaw and the outer jaw of each pair of clamping surfaces may have indentations facing each other. The indentations of each pair of clamping jaws cooperate to form channels to accommodate rod-shaped fastening means such as, for example, bone pins, screws, rods, etc. There may be an increased clamping effect on the fastening means when the angle $\alpha$ of an arc of contact or wrap is more than about 180°. The angle $\alpha$ of the arc of contact or wrap defines the area of contact or interface between a fastening means and the clamping surfaces.

A channel may be formed between the indentations and may have an axis which may extend at an angle to the longitudinal axis of the rod, wherein the axis of the channel may be positioned a distance from the longitudinal axis of the rod. The channels may have a shape which may be cylindrical or prismatic. Each channel may have a clear width LW and a width B between the adjoining clamping jaws such that the ratio of B/LW may be between about 70% and about 90%. In an embodiment where angle $\alpha$ is more than about 180°, the width B may be smaller than the clear width LW.

Furthermore, each clamping jaw may have a borehole which may be coaxial with the longitudinal axis. The rod may have a radial clearance in the borehole of at least one of the inner and outer clamping jaw of each pair of clamping jaws. The rod may have a diameter d and the borehole may have a diameter D, wherein D may be larger than d. In particular, the ratio (D−d)/d may be between about 0.01 and about 0.10. Moreover, the rod may have at least one reduced dimension area, which may be an annular groove. The rod may have a thickness b at the reduced dimension area and the borehole may have a diameter D, wherein b may be smaller than D.

A disk may be used to separate the clamping jaws. The disk may be positionable adjacent the inner clamping jaw of the first and second pair of clamping jaws. The disc may be configured to be shiftable/moveable along the longitudinal axis of the rod.

An elastic element may be used to allow a fastening means to be inserted/snapped in between inner and outer clamping jaws of a pair of clamping jaws. At least one of the first and second elastic elements may be rod-shaped and may be solid or hollow. Moreover, at least one of the first and second elastic elements may comprise a pseudoelastic material. In some embodiments, at least one of the first and second elastic elements may be selected from the group consisting of polyether ketone and carbon fiber-reinforced polyether ketone. In other embodiments, at least one of the first and second elastic elements may be made of a memory metal alloy. For example, the memory metal alloy may be nitinol. In some embodiments, at least one of the first and second elastic elements may be made of a nickel titanium alloy wherein 45%<Ni<55%, 45%<Ti<55%. The memory metal alloy may have a transition temperature higher than about 50° C. In particular, the memory metal alloy may have a transition temperature higher than about 80° C., more preferably, higher than about 100° C. and, most preferably, higher than about 120° C. In some embodiments, at least one of the first and second elastic elements may be made of a material which has a nonlinear stress-strain curve.

Each pair of clamping jaws may be capable of a clamping action which may not be based on a memory effect. The clamp may have one or more clamping elements such as a nut, a screw and/or a head. In one embodiment, the rod may comprise a thread for receiving the nut.

BRIEF DESCRIPTION OF THE DRAWINGS

The clamp is explained in even greater detail in the following exemplary drawings. The clamp may be better understood by reference to the following drawings, wherein like references numerals represent like elements. The drawings are merely exemplary to illustrate the structure of the clamp and the illustrated and described features may be used singularly or in combination with other features and the invention should not be limited to the embodiments shown.

DETAILED DESCRIPTION OF THE INVENTION

Figure 1:
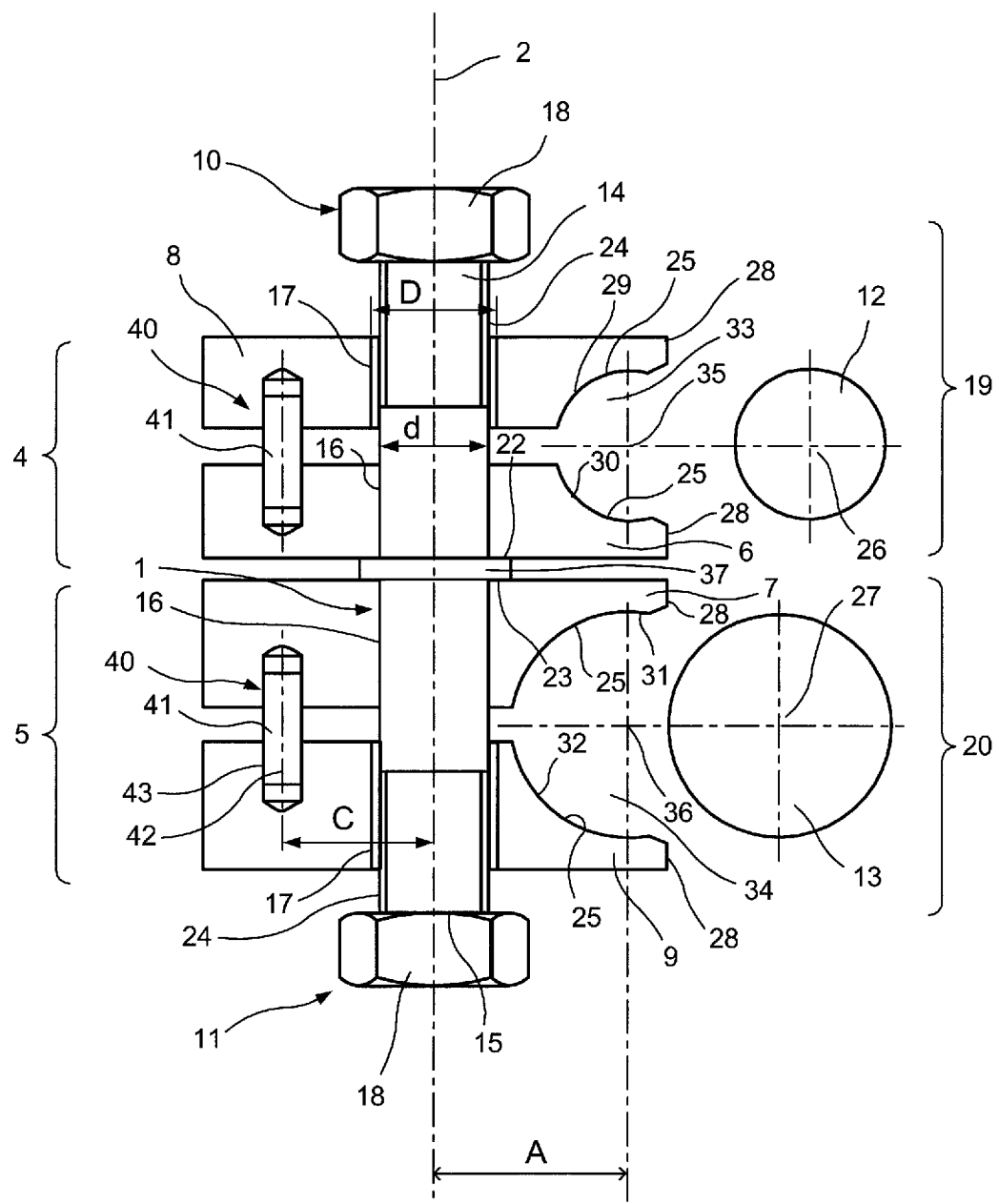
FIG. 1 is a cross-sectional view of the device of the present invention.

As shown in FIG. 1, the clamping device may include a rod 1 and a pair of clamping jaws 4, 5 which may be positioned on the rod 1. The clamping jaws 4, 5 may have inner clamping jaws 6, 7, respectively, and outer clamping jaws 8, 9, respectively. It should, however, be understood that those of ordinary skill in the art will recognize many modifications and substitutions which may be made to various elements of the clamping device.

The rod 1 may have two rod segments 19, 20 and a longitudinal axis 2. The rod 1 may be a single piece of material or may have multiple pieces. The pair of clamping jaws 4, 5 may be axially displaceable on each rod segment 19, 20, respectively. The clamping jaws 6, 7, 8, 9 may be shifted axially (i.e., axially displaceable) in pairs on the rod 1 and, in particular, on rod segments 19, 20. Furthermore, the clamping jaws 6, 7 and 8, 9 may be provided with boreholes 16, 17, respectively, which may be coaxial with the longitudinal axis 2. In one embodiment, the rod 1 may have radial clearance in the borehole 16, 17 so that at least one clamping jaw 6, 7, 8, 9 of each of the pairs of clamping jaws 4, 5 may be tilted from the position in which the clamping jaw 6, 7, 8, 9 may be coaxial with the longitudinal axis 2 of the rod 1. The clearance of the rod 1 may result from the difference between the dimensions of the rod 1 and the boreholes 16, 17. For example, the boreholes 16, 17 may have a diameter D and the rod 1 may have a diameter d such that the diameter D of the boreholes 16, 17 may be larger than the diameter d of the rod 1. The ratio of (D−d)/d may be between about 0.01 and about 0.10. In one embodiment, for example, where the diameter D of the borehole 17 of jaws 8 and 9 is greater than the diameter d of the rod 1, the jaws 6 and 8 of the first pair of clamping jaws 4 and jaws 7 and 9 of the second pair of clamping jaws 5 may be able to spread relative to each other.

The two clamping jaws 6, 8 of the first pair of clamping jaws 4 as well as the two clamping jaws 7, 9 of the second pair of clamping jaws 5 may each have a mutually opposite clamping surface 29, 30, 31, 32, which may be transverse to the longitudinal axis 2. Moreover, indentations 25 may be provided at each of two mutually opposite clamping surfaces 29, 30, 31, 32. The indentations 25 extend at an angle (e.g., orthogonal) to the longitudinal axis 2 and may be a distance from the longitudinal axis 2. The cross-sectional area of the indentations 25 may be approximately semi-circular in shape. In other embodiments, the cross-sectional area of the indentations 25 may be triangular.

Figure 2:
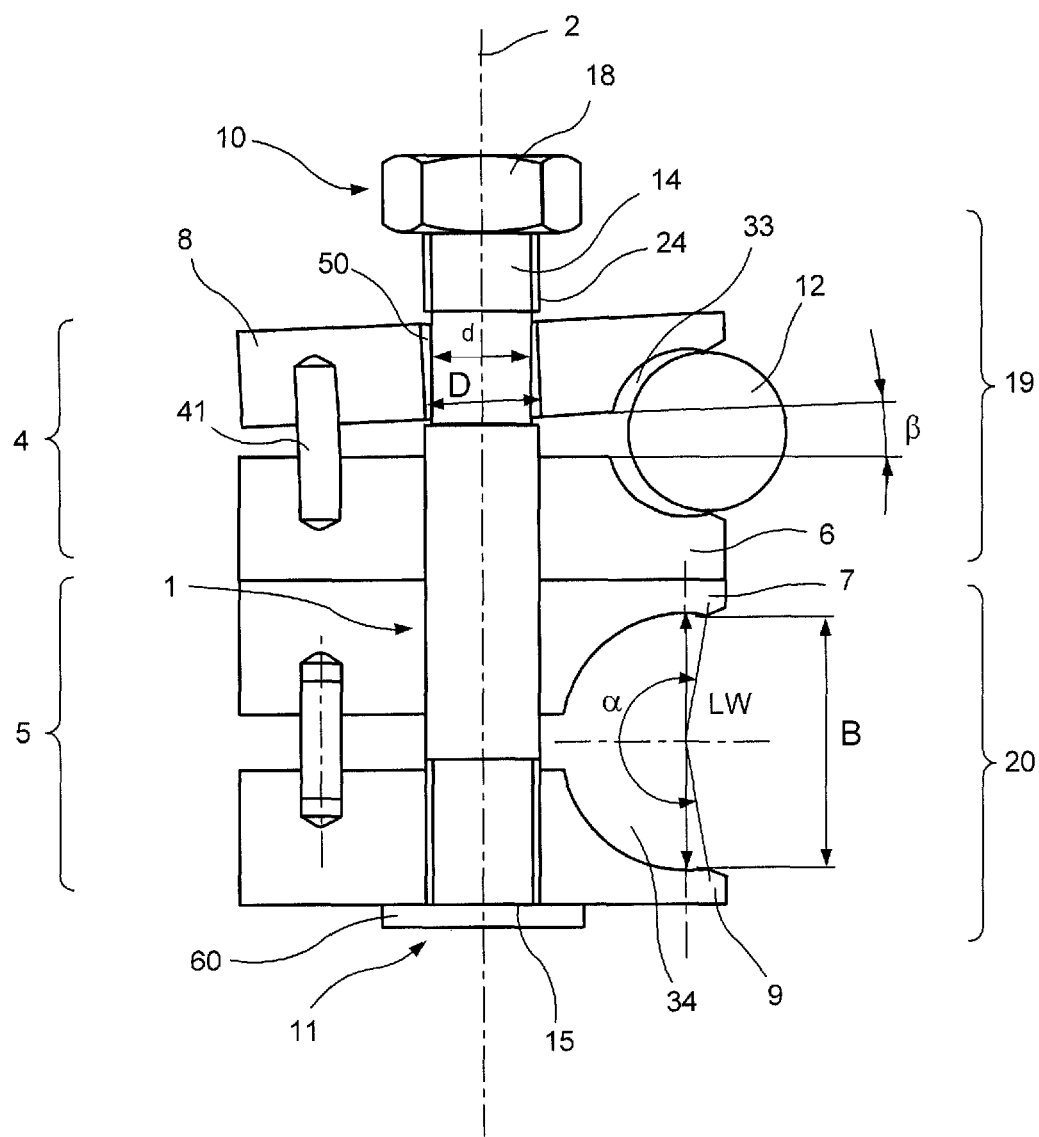
FIG. 2 is a cross-sectional view of an alternative embodiment of the device of the present invention.

The indentations 25 may form channels 33, 34 between the two clamping jaws 6, 7, 8, 9 of each pair of clamping jaws 4, 5. The channels 33, 34 may accommodate fastening means such as rod-shaped fastening means 12, 13, which may be pins, rods, shafts, screws, etc. The channels 33, 34 may be opened towards the side surfaces 28 of the clamping jaws 6, 7, 8, 9 and may have axes 35, 36, respectively, which may be at an angle (e.g., orthogonal) to, and spread a distance from the longitudinal axis 2. In one embodiment, the axes 35, 36 of the channels 33, 34 may be a distance A from the longitudinal axis 2. As shown in FIG. 2, the channels 33, 34 may have a clear width LW (i.e., the dimension or diameter of the channels 33, 34) which may be larger than the width B of the opening of the corresponding channel 33, 34 (i.e., the dimension between edges of the channels 33, 34), orthogonal to the respective channel axis 35, 36 at the side surfaces 28 of the clamping jaws 6, 7, 8, 9. Due to this configuration, the rod-shaped fastening means 12, 13, which may be inserted transversely to the longitudinal axis 2 into the channels 33, 34, may be secured from slipping out of the channels 33, 34. In one embodiment, the ratio B/LW of the minimum width B of a channel 33, 34 to the clear width LW of the same channel 33, 34 may be between about 70% and about 90%.

Moreover, the channels 33, 34 may be cylindrical or prismatic. In this way, an increased clamping effect on the rod-shaped fastening means 12, 13 may be generated. In particular, there may be an increased clamping effect on the rod-shaped fastening means 12, 13 when the angle α of an arc of contact or wrap is more than about 180° when viewed in a cross-section which is orthogonal to the channel axis 35, 36. The angle α of the arc of contact or wrap defines the area of contact or interface between a fastening means 12, 13 and the clamping surfaces 29, 30, 31, 32. In an embodiment where angle α is more than about 180°, the width B may be smaller than the clear width LW.

A rod-shaped fastening means 12, 13 may be inserted between the clamping surfaces 29, 30 of the pair of clamping jaws 4 and the clamping surfaces 31, 32 of the pair of clamping jaws 5. The fastening means 12, 13 may be inserted into the jaws 4, 5 in a direction which may be transverse to the longitudinal axis 2. When the clamping means 10, 11 are tightened, the fastening means 12 may be locked between an inner clamping jaw 6 and an outer clamping jaw 8, and the fastener 13 may be locked between an inner clamping jaw 7 and an outer clamping jaw 9.

In order to allow for the fastening means 12, 13 to be clipped into the jaws 4, 5 and in order to maintain a spaced axial relationship between the clamps jaws 6 and 8, 7 and 9, the jaws 4, 5 may be provide with elastic means 40. The distance between the two clamping jaws 6 and 8, 7 and 9, belonging to the pair of clamping jaws 4 and 5, respectively, may be such that rod-shaped fastening means 12, 13 may be moved by hand transversely to the longitudinal axis 2 between the two adjoining clamping surfaces 29 and 30, 31 and 32 of each pair of clamping jaws 4 and 5, respectively. With the clamping means 10, 11 in the loosened condition, the rod-shaped fastening means 12, 13 may be pushed in between jaws 6 and 8, 7 and 9. The fastening means 12, 13 may be clamped between the clamping surfaces 29, 30, 31, 32 by the elasticity of the elastic means 40. In the loosened condition, the fastening means 12, 13 may be shifted by hand parallel to central axes 26, 27, respectively. It will be appreciated that each clamping jaw 4, 5 may have an elastic means 40 so that independent operation of the two pairs of clamping jaws 4, 5 may be possible.

In one embodiment, the elastic means 40 may be disposed, with respect to the longitudinal axis 2, on the side of the clamping jaws 4, 5 opposite to the channels 33, 34, respectively. The elastic means 40 may be constructed as a rod-shaped element with a central axis 42 which may be parallel to the longitudinal axis 2 of the rod 1. The elastic means 40 may be at a distance from the longitudinal axis 2 of the rod 1. For example, there may be a distance C between the central axis 42 of the elastic means 40 and the longitudinal axis 2 of the rod 1. The elastic means 40 may be solid or hollow.

The elastic means 40 may consist of a material, which has a nonlinear stretch-strain curve. In one embodiment, the elastic means 40 may be produced from a memory metal alloy, for example, nitinol, without the clamping action of the elastic means 40 being based on the memory effect. In one embodiment, the elastic means 40 may consist of a nickel-titanium alloy, in which 45%<Ni<55%, 45% Ti<55% and x+y=100%. Such a material may be particularly biocompatible and highly elastic. The memory metal alloy may have a transition temperature of more than about 50° C. and, more preferably, more than about 80° C. In a related embodiment, the transition temperature may be more than about 100° C. and, preferably, more than about 120° C. In another embodiment, pseudo-elastic materials may also be suitable. Furthermore, in some embodiments, the elastic means 40 may consist of a plastic, preferably of a polyether ketone (PEEK) or a carbon fiber-reinforced PEEK.

The elastic means 40 may be a nitinol rod 41 which may have a central axis 42. A rod 41 may be inserted at a distance from rod 1 and between the two clamping jaws 6 and 8, 7 and 9 of each of the pairs of clamping jaws 4, 5. The rod 41 may be press-fit into bores 43 in the jaws 4, 5. In order to insert the rod-shaped fastening means 12, 13 into the channels 33, 34, respectively, the two corresponding clamping jaws 6 and 8, 7 and 9 of each pair of clamping tools 4 and 5, respectively, may be spread apart on sides 28. The jaws 6, 7, 8, 9 may be provided with the indentations 25 so that the two clamping jaws 6 and 8, 7 and 9 of each pair of clamping jaws 4 and 5, respectively, may be pressed against each other on the side of the elastic means 40, such that the elastic means (e.g., nitinol rods 41) may be deformed elastically. It should be noted that the elastic means 40 may be bendable as well as compressible.

As illustrated in FIG. 1, the inner clamping jaws 6, 7 may be positioned adjacent disk 37. The disk 37 may have end surfaces 22, 23 which engaged clamping jaws 6, 7, respectively. The disk 37 may be circular in shape, may be disposed between the rod segments 19, 20 and may be orthogonal to the longitudinal axis 2. In one embodiment, since the disk 37 may be firmly connected with the rod 1 between the first and the second rod segments 19, 20, the pair of clamping jaws 4, 5 may be separated so that the action of the clamping jaws 4, 5 may be independent of each other. In some embodiments, the disk 37 may have serrations (not shown) which may interact with serrations (not shown) on clamping jaws 6, 7 to fix the angular relative position of the clamping jaws 4, 5 with respect to each other.

In order to lock the position of the fixation means 12, 13 with respect to each other as well as the jaws 6, 7, 8, 9 with respect to each other, the device may incorporate clamping means 10, 11. The outer clamping jaws 8, 9 may be pressed by clamping means 10, 11 against the inner clamping jaws 6, 7. In one embodiment, the clamping means 10, 11 may be nuts 18, which may be screwed over terminally disposed threads 24 of the two rod segments 19, 20. In another embodiment, instead of the nut, a screw or bolt may be screwed into a borehole 16, 17 which may have an internal thread (not shown). In such an embodiment, the screw may be displaceable coaxially to the longitudinal axis 2 of the rod 1, or may be constructed as one piece with the rod 1. Moreover, the other clamping means may be a head 60 (FIG. 2), which may be firmly connected with the rod 1 or a second threaded connection.

Figure 3A:
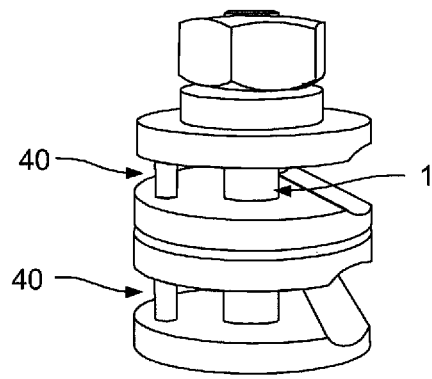
FIG. 3a is a side view of the device of FIG. 2.
Figure 3B:
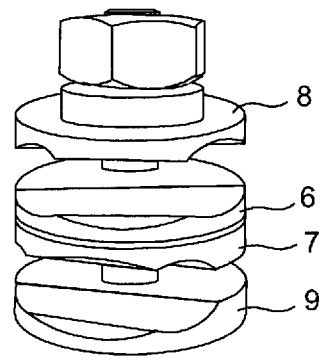
FIG. 3b is a front view of the device of FIG. 2.

FIGS. 2, 3a and 3b illustrates an embodiment where the first clamping means 10 may be constructed as a threaded connection with a nut 18. The nut 18 may be screwed over the thread 24 at the first end 14 of the rod 1. The second clamping means 11 may be a solid head 60 at the second end 15 of the rod 1. In such an embodiment, the outer clamping jaw 9 of the second pair of clamping jaws 5 may rest axially at the head 60. By tightening the first clamping means 10 (i.e., threading the nut 18 along the thread 24 towards the jaw 8), the two pairs of clamping jaws 4, 5 may be pressed together and positioned between the nut 18 and the head 60. In this way, the rod shaped fastening elements 12, 13, which have been inserted between the clamping jaws 6 and 8, 7 and 9 of each pair of clamping jaws 4, 5, may be clamped in the channels 33, 34.

As shown in FIG. 2, in order to spread apart the outer clamping jaws 8, 9 of each pair of clamping jaws 4, 5, respectively, when introducing the rod-shaped fastening means 12, 13, a reduced dimension area 50, which may be in the form of an annular groove may be provided along the rod 1 and may be located in the axial region of the outer clamping jaw 8, 9. The thickness b of the rod 1 at the reduced dimension area 50 may be smaller than the diameter D of the borehole 17 in the respective outer clamping jaw 8, 9.

In use, the rod-shaped fastening element 12, 13 may be pushed transversely to the longitudinal axis of the channels 32, 33, respectively, so that the jaws 6 and 8, 7 and 9 may form an angle therebetween. For example, the fastening element 12 may be pushed transversely to the longitudinal axis 2 into the channel 33. The two clamping jaws 6 and 8, adjoining the channel 33, may thereby be spread apart, for example, at an angle β of not more than between about 2° and about 3°.

While the foregoing description and drawings represent the preferred embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are therefore to be considered in all respects as illustrative and not restrictive, the scope of the invention being indicated by the appended claims, and not limited to the foregoing description.

What is claimed is:

1. A clamping device, comprising:
   a rod extending along a longitudinal axis from a first end to a second end;
   a first pair of clamping jaws operably associated with the rod, the first pair of clamping jaws having an inner clamping jaw and an outer clamping jaw, each of the inner clamping jaw and the outer clamping jaw including a bore extending therein parallel to and spaced a distance from the longitudinal axis of the rod, the first pair of clamping jaws defining a fastening element receiving channel extending therebetween transverse to the rod;
   a second pair of clamping jaws operably associated with the rod, the second pair of clamping jaws having an inner clamping jaw and an outer clamping jaw; and
   at least a first elastic element positioned in the bore between the inner and outer clamping jaws of the first pair of clamping jaws such that the first elastic element has a longitudinal axis which is parallel to and spaced a distance from the longitudinal axis of the rod on a side of the longitudinal axis opposite the fastening element receiving channel, the first elastic element being bendable so that the inner and outer clamping jaws of the first pair of clamping jaws are movable relative to one another.

2. The device of claim 1, wherein each clamping jaw has a borehole which is coaxial with the longitudinal axis of the rod.

3. The device of claim 2, wherein the rod has a diameter d and the borehole has a diameter D and wherein the ratio (D−d)/d is between about 0.01 and about 0.10.

4. The device of claim 1, wherein the rod has at least one reduced dimension area.

5. The device of claim 4, wherein the at least one reduced dimension area is an annular groove.

6. The device of claim 1, further comprising a disk positionable adjacent the inner clamping jaw of the first and second pair of clamping jaws.

7. The device of claim 6, wherein the disk is configured to be moveable along the longitudinal axis of the rod.

8. The device of claim 1, wherein the inner and outer clamping jaws of each pair of clamping jaws have indentations facing each other defining the fastening element receiving channel.

9. The device of claim 8, wherein each channel has edges and a clear width LW and a width B between the adjoining clamping jaws, wherein the clear width LW is the diameter of the channel and the width B is the dimension between the edges of the channel, wherein the ratio of B/LW is between about 70% and about 90%.

10. The device of claim 1 further comprising a second elastic element positioned between the inner and outer clamping jaws of the second pair of clamping jaws.

11. The device of claim 10, wherein each of the inner clamping jaw and the outer clamping jaw of the second pair of clamping jaws has a bore, wherein the bores receive the second elastic element.

12. The device of claim 10, wherein at least one of the first and second elastic elements is rod-shaped.

13. The device of claim 10, wherein at least one of the first and second elastic elements comprises a pseudoelastic material.

14. The device of claim 10, wherein the at least one of the first and second elastic elements is made of a material which has a nonlinear stress-strain curve.

15. The device of claim 10, wherein at least one of the first and second elastic elements is made of a memory metal alloy.

16. The device of claim 15, wherein the memory metal alloy is nitinol.

17. The device of claim 15, wherein the memory metal alloy has a transition temperature higher than about 50° C.

18. The device of claim 17, wherein the transition temperature is higher than about 120° C.

19. The device of claim 10, wherein at least one of the first and second elastic elements is made of a nickel titanium alloy wherein 45% <Ni <55%, 45% <Ti <55%.

20. The device of claim 10, wherein at least one of the first and second elastic elements is selected from the group consisting of polyether ketone and carbon fiber-reinforced polyether ketone.

21. The device of claim 1, wherein each pair of clamping jaws is capable of a clamping which action is not based on a memory effect.

22. The device of claim 1 further comprising a clamping element, wherein the clamping element is selected from the group consisting of a nut, a screw and a head.

23. The device of claim 22, wherein the rod comprises a thread for receiving the nut.

24. The device of claim 1, wherein the rod comprises multiple pieces.

25. The device of claim 1 further comprising an angle α of an arc of wrap, wherein the angle α of the arc of wrap defines an area of contact between a fastening means and inner and outer clamping jaws of one of the first and second pair of clamping jaws.

26. The device of claim 25, wherein the angle α is more than about 180°.

27. A clamping device, comprising:
   a rod extending along a longitudinal axis from a first end to a second end;
   a first pair of clamping jaws having an inner clamping jaw and an outer clamping jaw, each clamping jaw having a borehole receiving the rod, wherein each clamping jaw has an indentation on a first side of the longitudinal axis of the rod, the corresponding indentations forming a channel to receive a first fastening element, wherein the inner clamping jaw and the outer clamping jaw of first pair of clamping jaws each have a bore on a second side of the longitudinal axis of the rod opposite the indentation, the bore having a central axis substantially parallel to and spaced from a central axis of the borehole that receives the rod;
   a second pair of clamping jaws having an inner clamping jaw and an outer clamping jaw, each clamping jaw having a borehole receiving the rod, wherein each clamping jaw has an indentation on a first side of the clamping jaw, the corresponding indentations forming a channel to receive a second fastening element; and a first elastic element having a longitudinal axis, the first elastic element positioned between the inner and outer clamping jaws of the first pair of clamping jaws and in the respective bores of the inner and outer clamping jaws, the first elastic element being bendable so that the inner and outer clamping jaws of the first pair of clamping jaws are movable relative to one another.

28. The device of claim 27, wherein the inner clamping jaw and the outer clamping jaw of second pair of clamping jaws each have a bore on a second side of the clamping jaw opposite the indentation, the bore having an axis substantially parallel to and spaced from the borehole that receives the rod; and a second elastic element having an axis, the second elastic element positioned between the inner and outer clamping jaws of the second pair of clamping jaws, and in the respective bores of the inner and outer clamping jaws.

29. The device of claim 27 further comprising a disk positionable between the first and second pair of clamping jaws.

* * * * *